United States Patent [19]

Rubin et al.

[11] 4,209,499

[45] Jun. 24, 1980

[54] CRYSTALLINE ZEOLITE ZSM-43 SYNTHESIS THEREOF

[75] Inventors: Mae K. Rubin, Bala Cynwyd, Pa.; Edward J. Rosinski, Pedricktown; Charles J. Plank, Woodbury, both of N.J.

[73] Assignee: Mobil Oil Corporation, New York, N.Y.

[21] Appl. No.: 844,168

[22] Filed: Oct. 21, 1977

[51] Int. Cl.$^2$ .............................................. C01B 33/28
[52] U.S. Cl. .................................. 423/328; 252/455 Z; 260/448 C; 423/329
[58] Field of Search ...................... 423/328, 329, 330; 260/448 C; 252/431 N, 455 Z

[56] References Cited

U.S. PATENT DOCUMENTS

| | | | |
|---|---|---|---|
| 3,702,886 | 11/1972 | Argauer et al. | 423/328 |
| 3,832,449 | 8/1974 | Rosinski et al. | 423/328 |
| 3,904,738 | 9/1975 | Robson | 423/328 |
| 4,046,859 | 9/1977 | Plank et al. | 423/328 |

*Primary Examiner*—Edward J. Meros
*Attorney, Agent, or Firm*—C. A. Huggett; M. G. Gilman; R. W. Barclay

[57] ABSTRACT

A new crystalline zeolite, designated ZSM-43, a method of making same and the use thereof in catalytic conversion of organic compounds is the subject of this application. The new zeolite has a composition, in the anhydrous state, expressed in terms of mole ratios of oxides, as follows:

$$(0.6 \text{ to } 2.1)M_{2/n}O : Al_2O_3 : xSiO_2$$

wherein M is at least one cation having a valence n and x is at least 5, and is characterized by a specified X-ray powder diffraction pattern.

20 Claims, No Drawings

CRYSTALLINE ZEOLITE ZSM-43 SYNTHESIS THEREOF

BACKGROUND OF THE INVENTION

1. Field of the Invention

This invention relates to a novel crystalline aluminosilicate, to a method for its preparation and to its use in catalytic conversion of organic compounds.

2. Description of the Prior Art

Zeolitic materials, both natural and synthetic, have been demonstrated in the past to have catalytic properties for various types of hydrocarbon conversions. Certain zeolitic materials are ordered, porous crystalline aluminosilicates having a definite crystalline structure within which there are a large number of smaller cavities which may be interconnected by a number of still smaller channels. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as a rigid three-dimensional framework of $SiO_4$ and $AlO_4$ in which the tetrahedra are cross-linked by the sharing of oxygen atoms whereby the ratio of the total aluminum and silicon atoms to oxygen is 1:2. The electrovalence of the tetrahedra containing aluminum is balanced by the inclusion in the crystal of a cation, for example, an alkali metal or an alkaline earth metal cation. This can be expressed wherein the ratio of aluminum to the number of various cations, such as Ca, Sr, Na, K or Li is equal to unity. One type of cation may be exchanged either entirely or partially by another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic aluminosilicates. These aluminosilicates have come to be designated by letter or other convenient symbols, as illustrated by zeolite A (U.S. Pat. No. 2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752) and zeolite ZSM-5 (U.S. Pat. No. 3,702,886) merely to name a few.

SUMMARY OF THE INVENTION

The present invention relates to novel synthetic crystalline aluminosilicate, hereinafter designated "zeolite ZSM-43" or simply "ZSM-43", to a method for its preparation and to the conversion of organic compounds contacted therewith. The ZSM-43 composition has a characteristic X-ray diffraction pattern, the values of which are set forth in Table I, hereinafter. The ZSM-43 composition can also be identified, in terms of mole ratios of oxides and in the anhydrous state, as follows:

(0.6 to 2.1)$M_{2/n}O$: $Al_2O_3$:x$SiO_2$ wherein M is at least one cation, n is the valence thereof and x is at least 5. It will be noticed that the ratio of $M_{2/n}O$ may exceed unity in this material. This is probably due to the occlusion of excess organic species used in the preparation of ZSM-43 within the zeolite pores.

In a preferred synthesized form, the zeolite has a formula, in terms of mole ratios of oxides and in the anhydrous state, as follows:

(0.3 to 1.0)$Cs_2O$:(0 to 0.1)$Na_2O$:(0.3 to 1.0)$R_2O$:$Al_2O_3$:(5 to 20)$SiO_2$ wherein R is a nitrogen-containing organic cation.

In a more preferred synthesized form, the zeolite has a formula, in terms of mole ratios of oxides and in the anhydrous state, as follows:

(0.3 to 0.7)$Cs_2O$:(0.01 to 0.05)$Na_2O$:(0.3 to 0.7)$R_2O$:$Al_2O_3$:(9 to 17)$SiO_2$ wherein R is a nitrogen-containing organic cation, such as, for example, that derived from a 2-(hydroxyalkyl)-trialkylammonium compound, the alkyl groups of which are methyl, ethyl or a combination thereof.

The original cations of the as synthesized ZSM-43 can be replaced in accordance with techniques well known in the art, at least in part, by ion exchange with other cations. Ion exchange can be facilitated by prior calcination to remove organic species contained in the zeolite as synthesized. Preferred replacing cations include metal ions, ammonium ions, hydrogen ions and mixtures thereof. Particularly preferred cations are those which render the zeolite catalytically active especially for hydrocarbon coversion. These include hydrogen, rare earth metals and metals of Groups IIA, IIIA, IVA, IB, IIB, IIIB, IVB, VIB and VIII of the Periodic Table of Elements.

The synthetic ZSM-43 zeolite possesses a definite distinguishing crystalline structure whose X-ray diffraction pattern shows substantially the significant lines set forth in Table I.

TABLE I

| d(Å) | I/Io |
|---|---|
| 9.8 ± .2 | Weak |
| 7.6 ± .1 | Weak–Strong |
| 6.8 ± .1 | Medium–Very Strong |
| 6.0 ± .1 | Weak–Medium |
| 4.75 ± .1 | Medium–Very Strong |
| 3.78 ± .08 | Medium–Strong |
| 3.52 ± .07 | Medium |
| 3.31 ± .07 | Weak–Strong |
| 3.21 ± .06 | Medium–Very Strong |
| 3.06 ± .06 | Medium–Strong |
| 2.84 ± .06 | Weak–Medium |
| 2.57 ± .05 | Weak |
| 2.52 ± .05 | Weak–Medium |

These values were determined by standard technique. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 I/Io, where Io is the intensity of the strongest line or peak, and d (obs.), the interplanar spacing in Angstron units, corresponding to the recorded lines, were calculated. It should be understood that this X-ray diffraction pattern is characteristic of all the species of ZSM-43 compositions. Ion exchange of the original sodium or cesium ions with cations reveals substantially the same pattern with some minor shifts in interplanar spacing and variation in relative intensity. Other minor variations can occur depending on the silicon to aluminum ratio of the particular sample, as well as if it has previously been subjected to thermal treatment.

While synthetic ZSM-43 zeolite may be used in a wide variety of organic compound conversion reactions, it is notably useful in the processes of polymerization, aromatization, reforming, esterification and cracking. Other hydrocarbon conversion processes for which ZSM-43 may be utilized in one or more of its active forms include, for example, hydrocracking and converting light aliphatics to aromatics such as in U.S. Pat. No. 3,760,024.

Synthetic ZSM-43 zeolite can be used either in the alkali metal containing form, the alkali metal form and hydrogen form or another univalent or multivalent cationic form or combinations thereof. It can also be used in intimate combination with a hydrogenating component such as tungsten, vanadium, molybdenum, rhenium, nickel, chromium, manganese, or a noble metal such as platinum or palladium where a hydrogenation-dehydrogenation function is to be performed. Combinations of the aforenoted metals may also be used. Such components can be exchanged into the composition, impregnated thereon or physically intimately admixed therewith. Such components can be impregnated in or on to ZSM-43 such as, for example, by, in the case of platinum, treating the zeolite with a platinum metal-containing ion. Thus, suitable platinum compounds for this purpose include chloroplatinic acid, platinous chloride and various compounds containing the platinum amine complex. Combinations of metals and methods for their introduction can also be used.

As prepared, R can be a cation predominantly derived from 2-(hydroxyalkyl)trialkylammonium compounds, the alkyl groups of which are methyl, ethyl or combinations thereof, such as, for example, 2-(hydroxyethyl)trimethylammonium chloride. Non-limiting examples of such compounds include the halides, e.g. chlorides, fluorides and bromides, the sulfates, the acetates, the nitrates and others.

Synthetic ZSM-43, when employed either as an adsorbent or as a catalyst in a hydrocarbon conversion process, should be dehydrated at least partially. This can be done by thermal treatment, i.e. heating, to a temperature in the range of 50° C. to about 900° C. in an atmosphere such as air, nitrogen, etc. and at atmospheric or subatmospheric pressures for between 1 and 48 hours. Dehydration can also be performed at lower temperature merely by placing the zeolite in a vacuum, but a longer time is required to obtain a sufficient amount of dehydration.

Zeolite ZSM-43 can be suitably synthesized by preparing a solution containing sources of sodium oxide, cesium oxide, nitrogen-containing organic cations, preferably a 2-(hydroxyalkyl)trialkylammonium compound, aluminum oxide, silicon dioxide and water and having a composition, in terms of mole ratios of oxides, falling within the following ranges:

|  |  | Broad | Optimum |
|---|---|---|---|
| $R^+/(R^+ + Na^+ + Cs^+)$ | = | 0.2–0.7 | 0.4–0.6 |
| $OH^-/SiO_2$ | = | 0.3–0.7 | 0.3–0.6 |
| $H_2O/OH^-$ | = | 15–100 | 30–70 |
| $SiO_2/Al_2O_3$ | = | 8–25 | 10–20 |

-continued

|  |  | Broad | Optimum |
|---|---|---|---|
| $Cs_2O/(Na_2O + Cs_2O)$ | = | 0.1–1.0 | 0.2–0.6 | wherein R is as above defined, and maintaining the mixture until crystals of the zeolite are formed. Thereafter, the crystals are separated from the liquid by, for example, cooling the whole to room temperature, filtering and water washing; and are dried. Typical reaction conditions consist of heating the foregoing reaction mixture to a temperature of from about 80° C. to about 220° C. for a period of time of from about 20 hours to about 170 days. A more preferred temperature range is from about 120° C. to about 150° C. with the amount of time at a temperature in such range being from about 24 hours to about 27 days.

The composition for the synthesis of synthetic ZSM-43 can be prepared utilizing materials which can supply the appropriate oxide. Such compositions include aluminates, alumina, silicates, silica hydrosol, silica gel, silicic acid and hydroxides. It will be understood that each oxide component utilized in the reaction mixture for preparing ZSM-43 can be supplied by one or more essential reactants and they can be mixed together in any order. For example, any oxide can be supplied by an aqueous solution, sodium hydroxide or by an aqueous solution of a suitable silicate. The silicon dioxide reactant may be a finely dispersed, highly reactive silica such as obtained by precipitation from an aqueous solution of a silicate or by vapor-phase hydrolysis of a silicon halide, e.g. chloride or bromide. The silicon dioxide may also be provided as a colloidal silica sol. The reaction mixture can be prepared either batchwise or continuously. Crystal size and crystallization time of the ZSM-43 composition will vary with the nature of the reaction mixture employed.

DESCRIPTION OF SPECIFIC EMBODIMENTS

As above mentioned, synthetic ZSM-43 can have the original sodium ions associated therewith replaced by a wide variety of other cations according to techniques well known in the art. Typical replacing cations include hydrogen, ammonium and metal cations including mixtures thereof. Of the replacing metallic cations, particular preference is given to cations of metals such as rare earth, Mn, Ca, Mg, Zn, Cd, Pd, Ni, Co, Ti, Al, Sn, Fe and Cu.

A typical ion exchange technique would be to contact the synthetic ZSM-43 zeolite with a salt of the desired replacing cation or cations. Although a wide variety of salts can be employed, particular preference is given to chlorides, nitrates and sulfates.

Representative ion exchange techniques are disclosed in a wide variety of patents including U.S. Pat. Nos. 3,140,249; 3,140,251; and 3,140,253.

Following contact with the salt solution of the desired replacing cation, the zeolite is then preferably washed with water and dried at a temperature ranging from 50° C. to about 300° C. and thereafter may be calcined in air or other inert gas at from about 200° C. to a temperature below the zeolite decomposition temperature, preferably about 900° C., for periods of time ranging from 1 to 48 hours or more to produce a catalytically-active thermal decomposition product thereof.

Regardless of the cations replacing the sodium or cesium ions in the synthesized form of the ZSM-43, the spacial arrangement of the aluminum, silicon and oxygen atoms which form the basic crystal lattice of ZSM-43 remains essentially unchanged by the described replacement of alkali metal as determined by taking an X-ray powder diffraction pattern of the ion-exchanged material.

The aluminosilicate prepared by the instant invention is formed in a wide variety of particle sizes. Generally speaking, the particles can be in the form of a powder, a granule, or a molded product, such as extrudate having particle size sufficient to pass through a 2 mesh (Tyler) screen and be retained on a 400 mesh (Tyler) screen. In cases where the catalyst is molded, such as by extrusion, the aluminosilicate can be extruded before drying or dried or partially dried and then extruded.

In the case of many catalysts, it is desired to incorporate the ZSM-43 with another material resistant to the temperatures and other conditions employed in organic conversion processes. Such matrix materials include active and inactive materials and synthetic or naturally occurring zeolites as well as inorganic materials such as clays, silica and/or metal oxides. The latter may be either naturally occurring or in the form of gelatinous precipitates, sols or gels including mixtures of silica and metal oxides. Use of a material in conjunction with the ZSM-43, i.e. combined therewith, which is active, tends to improve the conversion and/or selectivity of the catalyst in certain organic conversion processes. Inactive materials suitably serve as diluents to control the amount of conversion in a given process so that products can be obtained economically and orderly without employing other means for controlling the rate of reaction. Frequently, zeolite materials have been incorporated into naturally occurring clays, e.g. bentonite and kaolin. These materials, i.e. clays, oxides, etc., function, in part, as binders for the catalyst. It is desirable to provide a catalyst having good crush strength, because in a petroleum refinery the catalyst is often subjected to rough handling, which tends to break the catalyst down into powder-like materials which cause problems in processing.

Naturally occurring clays which can be composited with the synthetic ZSM-43 catalyst include the montmorillonite and kaolin families which include the sub-bentonites and the kaolins commonly known as Dixie, McNamee, Georgia and Florida clays or others in which the main mineral constituents is halloysite, kaolinite, dickite, nacrite, or anauxite. Such clays can be used in the raw state as originally mined or initially subjected to calcination, acid treatment or chemical modification.

In addition to the foregoing materials, the ZSM-43 catalyst can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used. The relative proportions of finely divided crystalline aluminosilicate ZSM-43 and inorganic oxide gel matrix vary widely with the crystalline aluminosilicate content ranging from about 1 to about 90 percent by weight and more usually in the range of about 2 to about 70 percent by weight of the composite.

For conversion of organic compounds in general, the organic compound of feedstock containing same may be contacted with a catalyst containing the zeolite ZSM-43 at a temperature between about 37° C. and about 760° C., a pressure between about atmospheric and about 200 atmospheres, a hydrogen/organic compound mole ratio of between 0 and about 80, and a weight hourly space velocity (WHSV) of from about 0.1 $hr^{-1}$ to about 1000 $hr^{-1}$.

More specifically, when said conversion involves polymerization of olefin-containing liquid or gaseous feedstocks the temperature will be between about 260° C. and about 482° C., the pressure will be from about atmospheric to about 50 atmospheres and the WHSV will be from about 0.5 $hr^{-1}$ to about 50 $hr^{-1}$. When said conversion is the alkylation of aromatics, such as benzene or toluene, with an alkylating agent of an olefin or alcohol, reaction conditions will include a temperature of from about 204° C. to about 538° C., a pressure of from about atmospheric to about 60 atmospheres, a WHSV of from about 0.5 $hr^{-1}$ to about 50 $hr^{-1}$ and an aromatic compound/alkylating agent mole ratio of from about 2 to about 200. When said conversion is isomerization of aromatics such as xylenes, reaction conditions will include a temperature of from about 148° C. to about 482° C., a pressure of from atmospheric to about 60 atmospheres, and a WHSV of from about 0.2 $hr^{-1}$ to about 100 $hr^{-1}$. When said conversion is isomerization of paraffins or olefins, reaction conditions will include a temperature of from about 37° C. to about 371° C., a pressure of from atmospheric to about 60 atmospheres, and a WHSV of from about 0.1 $hr^{-1}$ to about 2 $hr^{-1}$. When said conversion is disproportionation of aromatics, such as toluene, reaction conditions will include a temperature of from about 315° C. to about 621° C., a pressure of from atmospheric to about 50 atmospheres, and a WHSV of from about 0.5 $hr^{-1}$ to about 20 $hr^{-1}$. When said conversion is transalkylation of aromatics, such as benzene, with alkylaromatics, such as trimethylbenzenes, reaction conditions will include a temperature of from about 260° C. to about 593° C., a pressure of from atmospheric to about 50 atmospheres, and a WHSV of from about 0.1 $hr^{-1}$ to about 1000 $hr^{-1}$.

In order to more fully illustrate the nature of the invention and the manner of practicing same, the following examples are presented.

In the examples which follow, whenever adsorption data are set forth for comparison of sorptive capacities for water, cyclohexane and n-hexane, they were determined as follows:

A weighed sample of the calcined zeolite was contacted with the desired pure adsorbate vapor in an adsorption chamber, evacuated to 12 mm when checking capacity for water and 20 mm when checking capacity for cyclohexane and n-hexane, pressure less than the vapor-liquid equilibrium pressure of the respective adsorbate at room temperature. The pressure was kept constant (within about ±0.5 mm) by addition of adsorbate vapor controlled by a manostat during the adsorption period which did not exceed about eight hours. As adsorbate was adsorbed by the zeolite, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample.

EXAMPLES 1-4

Four separate reaction mixtures for synthesis of zeolite ZSM-43 were prepared as indicated in Table II. The sodium aluminate used in the compositions was composed of 43.3 wt. % $Al_2O_3$, 32.2 wt. % $Na_2O$ and 24.5 wt. % water. The colloidal silica used in Examples 1, 2 and 3 contained 30 wt. % $SiO_2$ and 70 wt. % water. The silica used in Example 4 was 91.3 wt. % precipitated hydrated $SiO_2$ having a particle size of about 0.02 micron and 8.7 wt. % water. The nitrogen-containing organic compound was choline chloride, i.e. 2-(hydroxyethyl)trimethylammonium chloride. Crystallizations were carried out at 99° C. for Examples 1 and 2 for 145 days and 170 days, respectively; and at 149° C. for Example 3 and 4, for 20 days and 27 days, respectively. The crystalline products formed from the reaction mixtures were separated therefrom by filtration, water-washed and then dried at 110° C. for 16 hours.

The zeolite products of these examples were determined by X-ray diffraction analysis to be ZSM-43. They were subjected to analysis for product composition and adsorption and surface area evaluations. Product compositions, adsorption and surface area data are listed in Table III. X-ray diffraction data for the product zeolites are listed in Tables IV-VII.

TABLE II

Reaction Mixture Compositions

| Example | 1 | 2 | 3 | 4 |
|---|---|---|---|---|
| Components, grams: | | | | |
| Sodium Aluminate | 11.8 | 11.8 | 5.9 | 5.9 |
| NaOH | 2.2 | 2.2 | 1.1 | 2.2 (50 wt. % solution) |
| CsOH | 14.0 | 14.0 | 7.0 | 7.0 |
| Water | 130.0 | 130.0 | 65.0 | 106.0 |
| Colloidal $SiO_2$ | 130.0 | 130.0 | 65.0 | — |
| Precipitated $SiO_2$ | — | — | — | 21.4 |
| Choline Chloride | 38.0 | 38.0 | 19.0 | 19.0 |
| Starting Composition molar ratios: | | | | |
| $R^+/(R^+ + Na^+ + Cs^+)$ | 0.50 | 0.50 | 0.50 | 0.50 |
| $OH^-/SiO_2$ | 0.42 | 0.42 | 0.42 | 0.42 |
| $H_2O/OH^-$ | 45.5 | 45.5 | 45.5 | 43.9 |
| $SiO_2/Al_2O_3$ | 13.0 | 13.0 | 13.0 | 13.0 |
| $Cs_2O/(Na_2O + Cs_2O)$ | 0.34 | 0.34 | 0.34 | 0.34 |
| Crystallization Temp., °C. | 98.9 | 98.9 | 148.9 | 148.9 |
| Time, days | 145 | 170 | 20 | 27 |

TABLE III

Zeolite Product Properties

| Example | 1 | 2 | 3 | 4 |
|---|---|---|---|---|
| Product Composition, wt. %: | | | | |
| N | 1.21 | 1.30 | 1.31 | 1.34 |
| Na | 0.10 | 0.07 | 0.13 | 0.15 |
| Cs | 19.0 | 10.2 | 13.0 | 13.2 |
| $Al_2O_3$ | 12.1 | 10.4 | 8.3 | 9.1 |
| $SiO_2$ | 70.5 | 67.6 | 78.3 | 73.3 |
| Product Composition, moles: | | | | |
| $Al_2O_3$ | 1 | 1 | 1 | 1 |
| $SiO_2$ | 9.8 | 11.1 | 16.1 | 13.7 |
| $Cs_2O$ | 0.60 | 0.38 | 0.60 | 0.56 |
| $R_2O$ | 0.41 | 0.50 | 0.67 | 0.60 |
| $Na_2O$ | 0.02 | 0.02 | 0.03 | 0.04 |
| Adsorption*, wt. %: | | | | |
| Cyclohexane | 5.0 | 2.2 | 4.0 | 6.4 |
| n-Hexane | 6.2 | 5.2 | 6.3 | 4.8 |
| Water | 10.2 | 16.0 | 23.0 | 14.7 |
| Surface Area, m²/gram | 379 | 363 | 342 | 288 |

*Zeolite calcined for 16 hours at 1000° F.

TABLE IV

X-Ray Diffraction Pattern Data Generated By The Zeolite Product of Example 1

| 2 × theta | d(Å) | I/Io |
|---|---|---|
| 6.00 | 14.73 | 22 |
| 8.90 | 9.94 | 6 |
| 11.70 | 7.56 | 65 |
| 12.30 | 7.20 | 8 |
| 12.90 | 6.86 | 31 |
| 13.52 | 6.55 | 7 |
| 14.84 | 5.97 | 2 |
| 17.52 | 5.06 | 6 |
| 18.66 | 4.75 | 100 |
| 19.96 | 4.45 | 5 |
| 21.60 | 4.11 | 5 |
| 23.44 | 3.80 | 62 |
| 24.36 | 3.65 | 26 |
| 25.25 | 3.53 | 30 |
| 26.05 | 3.42 | 52 |
| 26.93 | 3.31 | 59 |
| 27.73 | 3.22 | 92 |
| 29.08 | 3.07 | 49 |
| 30.70 | 2.912 | 22 |
| 31.42 | 2.847 | 28 |
| 34.77 | 2.580 | 11 |
| 35.50 | 2.529 | 24 |

TABLE V

X-Ray Diffraction Pattern Data Generated By The Zeolite Product of Example 2

| 2 × theta | d(Å) | I/Io |
|---|---|---|
| 6.10 | 14.49 | 23 |
| 8.98 | 9.85 | 11 |
| 11.68 | 7.58 | 58 |
| 12.30 | 7.20 | 9 |
| 12.87 | 6.88 | 34 |
| 13.50 | 6.56 | 5 |
| 14.78 | 5.99 | 3 |
| 17.53 | 5.06 | 6 |
| 18.63 | 4.76 | 100 |
| 19.73 | 4.50 | 4 |
| 21.49 | 4.13 | 3 |
| 23.47 | 3.79 | 58 |
| 25.27 | 3.52 | 28 |
| 26.08 | 3.42 | 12 |
| 26.92 | 3.31 | 52 |
| 27.73 | 3.22 | 85 |
| 29.04 | 3.07 | 49 |
| 30.51 | 2.930 | 9 |
| 31.38 | 2.851 | 27 |
| 34.72 | 2.584 | 10 |
| 35.46 | 2.531 | 24 |

TABLE VI

X-Ray Diffraction Pattern Data Generated
By The Zeolite Product of Example 3

| 2 × theta | d(Å) | I/Io |
|---|---|---|
| 6.34 | 13.94 | 17 |
| 9.00 | 9.83 | 9 |
| 11.73 | 7.54 | 40 |
| 12.33 | 7.18 | 3 |
| 12.92 | 6.85 | 26 |
| 13.40 | 6.61 | 6 |
| 14.88 | 5.95 | 4 |
| 17.58 | 5.04 | 2 |
| 18.73 | 4.74 | 100 |
| 19.94 | 4.45 | 3 |
| 21.86 | 4.07 | 3 |
| 23.58 | 3.77 | 53 |
| 24.58 | 3.62 | 9 |
| 25.40 | 3.51 | 30 |
| 26.18 | 3.40 | 17 |
| 26.98 | 3.30 | 40 |
| 27.85 | 3.20 | 63 |
| 29.22 | 3.06 | 45 |
| 30.10 | 2.969 | 6 |
| 30.77 | 2.906 | 5 |
| 31.50 | 2.840 | 23 |
| 34.92 | 2.569 | 11 |
| 35.61 | 2.521 | 15 |

TABLE VII

X-Ray Diffraction Pattern Data Generated
By The Zeolite Product of Example 4

| 2 × theta | d(Å) | I/Io |
|---|---|---|
| 6.32 | 13.98 | 22 |
| 7.55 | 11.71 | 3 |
| 9.08 | 9.74 | 12 |
| 11.70 | 7.56 | 43 |
| 12.48 | 7.09 | 6 |
| 12.94 | 6.84 | 26 |
| 13.39 | 6.61 | 5 |
| 14.83 | 5.97 | 6 |
| 17.57 | 5.05 | 3 |
| 18.70 | 4.74 | 100 |
| 19.76 | 4.49 | 5 |
| 20.67 | 4.30 | 4 |
| 21.82 | 4.07 | 5 |
| 23.59 | 3.77 | 61 |
| 24.50 | 3.63 | 10 |
| 25.33 | 3.52 | 31 |
| 26.27 | 3.39 | 16 |
| 26.97 | 3.31 | 40 |
| 27.81 | 3.21 | 62 |
| 28.57 | 3.12 | 9 |
| 29.23 | 3.06 | 50 |
| 30.08 | 2.971 | 9 |
| 30.77 | 2.906 | 9 |
| 31.52 | 2.838 | 25 |
| 34.92 | 2.569 | 12 |
| 35.61 | 2.521 | 16 |

EXAMPLE 5

A 16 gram quantity of the zeolite product of Example 1 was dried at 110° C. for 16 hours and then contacted five times for one hour each contacting with a 10 wt. % solution of NH$_4$Cl at about 88° C. The NH$_4$—exchanged zeolite ZSM-43 was determined to contain 0.03 wt. % Na and 12.6 wt. %. Cs.

EXAMPLE 6

After calcination for 10 hours at about 538° C., a 0.25 gram portion of the NH$_4$—exchanged zeolite ZSM-43 of Example 5 was placed in a small glass reaction vessel and contacted with propylene at a weight hourly space velocity of 6.2 hr$^{-1}$, a temperature of 315.5° C. and atmospheric pressure. After a one hour prerun period, a one hour balance run was made. Conversion of the propylene was measured to be 59.2 wt. % and the product was determined to include 96.4 wt. % C$_4^+$, 88.0 wt. % C$_5^+$ and 76.1 wt. % C$_6^+$ material. Less than 1 wt. % aromatics were formed along with about 3 wt. % propane.

EXAMPLE 7

The NH—exchanged ZSM-43 used in Example 6 was calcined at about 538° C. for ten hours and then contacted five times for one hour each contacting with a 10 wt. % solution of NH$_4$Cl at about 88° C. This re-exchanged zeolite ZSM-43 was determined to contain only 1.1 wt. % Cs. This zeolite exhibited the X-ray diffraction pattern data listed below:

| 2 × theta | d(Å) | I/Io |
|---|---|---|
| 6.10 | 14.49 | 5 |
| 8.90 | 9.94 | 5 |
| 11.70 | 7.56 | 3 |
| 12.95 | 6.84 | 100 |
| 13.65 | 6.49 | 15 |
| 14.32 | 6.18 | 17 |
| 14.92 | 5.94 | 21 |
| 17.53 | 5.06 | 3 |
| 18.68 | 4.75 | 29 |
| 19.73 | 4.50 | 4 |
| 20.46 | 4.34 | 5 |
| 21.80 | 4.08 | 2 |
| 23.53 | 3.78 | 35 |
| 24.46 | 3.64 | 27 |
| 25.32 | 3.52 | 37 |
| 26.33 | 3.38 | 13 |
| 26.96 | 3.31 | 16 |
| 27.80 | 3.21 | 36 |
| 29.23 | 3.06 | 34 |
| 30.60 | 2.921 | 8 |
| 31.36 | 2.852 | 11 |
| 34.90 | 2.571 | 4 |
| 35.62 | 2.520 | 9 |

EXAMPLE 8

After calcination for 10 hours at about 538° C., a 0.25 gram portion of the re-exchanged zeolite ZSM-43 of Example 7 was placed in the same reaction vessel used for Example 6 and contacted with propylene at a WHSV of 7.5 hr$^{-1}$, a temperature of 315.5° C. and atmospheric pressure. After a one hour prerun period a one hour balance run was made. Conversion of propylene was measured to be 15.8 wt. % and the product was determined to include 92.5 wt. % C$_4^+$ and 86.4 wt. % C$_5^+$ material.

EXAMPLE 9

A 19.5 gram quantity of the zeolite product of Example 3 was dried at 110° C. for 16 hours, calcined at 538° C. for 10 hours and then contacted five times for one hour each contacting with a 10 wt. % solution of NH$_4$Cl at about 88° C. The final zeolite product was thereafter determined to contain 1.8 wt. % Cs. This zeolite exhibited the X-ray diffraction pattern data listed below:

| 2 × theta | d(Å) | I/Io |
|---|---|---|
| 6.40 | 13.81 | 5 |
| 9.03 | 9.79 | 8 |
| 9.67 | 9.15 | 2 |
| 11.68 | 7.58 | 26 |
| 12.88 | 6.87 | 100 |

| 2 × theta | d(Å) | I/Io |
|---|---|---|
| 13.60 | 6.51 | 7 |
| 14.50 | 6.11 | 17 |
| 14.87 | 5.96 | 20 |
| 17.50 | 5.07 | 2 |
| 18.66 | 4.75 | 36 |
| 19.60 | 4.53 | 4 |
| 20.55 | 4.32 | 5 |
| 23.61 | 3.77 | 32 |
| 24.50 | 3.63 | 20 |
| 25.36 | 3.51 | 37 |
| 26.28 | 3.39 | 15 |
| 27.00 | 3.30 | 14 |
| 27.83 | 3.21 | 31 |
| 29.32 | 3.05 | 36 |
| 30.23 | 2.956 | 3 |
| 30.86 | 2.897 | 2 |
| 31.53 | 2.837 | 11 |
| 33.50 | 2.675 | 2 |
| 35.05 | 2.560 | 6 |
| 35.65 | 2.518 | 8 |
| 36.15 | 2.485 | 2 |

EXAMPLE 10

A 1.0 cc portion of the zeolite of Example 9 which had been calcined 10 hours at about 538° C. was placed in a small glass reactor and subjected to the standard n-hexane cracking (Alpha) test at 538° C. Helium was used as the carrier gas and the liquid hourly space velocity for the n-hexane was 1.0. The extent of n-hexane conversion was 2.6 wt. % after 5 minutes on stream. This calculated to a relative cracking activity of 0.51 compared to a standard silica-alumina cracking catalyst.

EXAMPLE 11

A 21.0 gram quantity of the zeolite product of Example 4 was dried at 110° C. for 16 hours, calcined at 538° C. for 10 hours and then contacted five times for one hour each contacting with a 10 wt. % solution of $NH_4Cl$ at about 88° C. The $NH_4$—exchanged ZSM-43 was thereafter determined to contain 2.2 wt. % Cs. This zeolite exhibited the X-ray diffraction pattern data listed below:

| 2 × theta | d(Å) | I/Io |
|---|---|---|
| 6.30 | 14.03 | 8 |
| 7.65 | 11.56 | 2 |
| 9.15 | 9.66 | 12 |
| 9.75 | 9.07 | 4 |
| 10.45 | 8.47 | 2 |
| 11.72 | 7.55 | 22 |
| 12.95 | 6.84 | 100 |
| 13.54 | 6.54 | 10 |
| 14.48 | 6.12 | 20 |
| 14.90 | 5.95 | 27 |
| 15.73 | 5.63 | 3 |
| 17.50 | 5.07 | 2 |
| 18.70 | 4.74 | 36 |
| 19.65 | 4.52 | 5 |
| 20.66 | 4.30 | 5 |
| 21.80 | 4.08 | 2 |
| 23.66 | 3.76 | 37 |
| 24.53 | 3.63 | 18 |
| 25.40 | 3.51 | 36 |
| 26.17 | 3.40 | 13 |
| 26.54 | 3.36 | 14 |
| 27.03 | 3.30 | 15 |
| 27.86 | 3.20 | 32 |
| 28.54 | 3.13 | 5 |
| 29.36 | 3.04 | 42 |
| 30.28 | 2.952 | 7 |
| 30.84 | 2.899 | 6 |
| 31.60 | 2.831 | 15 |
| 33.60 | 2.667 | 2 |
| 35.10 | 2.556 | 6 |
| 35.68 | 2.516 | 8 |
| 36.20 | 2.481 | 2 |

EXAMPLE 12

A 1.86 gram portion of the zeolite of Example 9, which had been calcined 10 hours at about 538° C., was tested for methanol conversion. The catalyst was placed in a small vertically mounted glass reaction tube and a mixture of 30 wt. % methanol in water was charged over the catalyst at an inlet temperature of 371° C. and a weight hourly space velocity of 3.07 $hr^{-1}$. After a prerun period of 45 minutes a balance run was made for one hour. The conversion of the methanol to hydrocarbon products was 41.7 wt. % of the theoretical maximum. Of the hydrocarbon products, about 43 wt. % was ethylene.

We claim:

1. A synthetic crystalline aluminosilicate zeolite having a composition in the anhydrous state, expressed in terms of mole ratios of oxides, as follows:

$$(0.6 \text{ to } 2.1)M_{2/n}O:Al_2O_3:xSiO_2$$

wherein M is at least one cation having a valence n and x is at least 5, said zeolite having the X-ray diffraction lines substantially as shown in Table I of the specification.

2. A synthetic crystalline aluminosilicate zeolite according to claim 1 having a composition in the anhydrous state, expressed in terms of mole ratios of oxides, as follows:

$$(0.3 \text{ to } 1.0)Cs_2O:(0 \text{ to } 0.1)Na_2O:(0.3 \text{ to } 1.0)R_2O:Al_2O_3:(5 \text{ to } 20)SiO_2$$

wherein R is a nitrogen-containing organic cation.

3. A synthetic crystalline aluminosilicate zeolite according to claim 2 having a composition in the anhydrous state, expressed in terms of mole ratios of oxides, as follows:

$$(0.3 \text{ to } 0.7)Cs_2O:(0.01 \text{ to } 0.05)Na_2O:(0.3 \text{ to } 0.7)R_2O:Al_2O_3:(9 \text{ to } 17)SiO_2$$

4. A crystalline aluminosilicate zeolite resulting from thermal treatment of the composition of claim 1.

5. A crystalline aluminosilicate zeolite resulting from thermal treatment of the composition of claim 2.

6. A crystalline aluminosilicate zeolite resulting from thermal treatment of the composition of claim 3.

7. The synthetic crystalline aluminosilicate zeolite according to claim 2 wherein R is the nitrogen-containing organic cation derived from a 2-(hydroxyalkyl)-trialkylammonium compound, the alkyl groups of which are methyl, ethyl or a combination thereof.

8. The synthetic crystalline aluminosilicate zeolite resulting from thermal treatment of the composition of claim 7.

9. A synthetic crystalline aluminosilicate zeolite comprising the zeolite of claim 1 having its original cations replaced, at least in part, with a cation or a mixture of cations selected from the group consisting of hydrogen and hydrogen precursors, rare earth metals and metals from Groups IIA, IIIA, IVA, IB, IIB, IIIB, IVB, VIB and VIII of the Periodic Table of the Elements.

10. A synthetic crystalline aluminosilicate zeolite comprising the zeolite of claim 2 having its original cations replaced, at least in part, with a cation or a mixture of cations selected from the group consisting of hydrogen and hydrogen precursors, rare earth metals and metals from Groups IIA, IIIA, IVA, IB, IIB, IIIB, IVB, VIB and VIII of the Periodic Table of the Elements.

11. A synthetic crystalline aluminosilicate zeolite comprising the zeolite of claim 3 having its original cations replaced, at least in part, with a cation or a mixture of cations selected from the group consisting of hydrogen and hydrogen precursors, rare earth metals and metals from Groups IIA, IIIA, IVA, IB, IIB, IIIB, IVB, VIB and VIII of the Periodic Table of the Elements.

12. A synthetic crystalline aluminosilicate zeolite comprising the zeolite of claim 4 having its original cations replaced, at least in part, with a cation or a mixture of cations selected from the group consisting of hydrogen and hydrogen precursors, rare earth metals and metals from Groups IIA, IIIA, IVA, IB, IIB, IIIB, IVB, VIB and VIII of the Periodic Table of the Elements.

13. A synthetic crystalline aluminosilicate zeolite comprising the zeolite of claim 5 having its original cations replaced, at least in part, with a cation or a mixture of cations selected from the group consisting of hydrogen and hydrogen precursors, rare earth metals and metals from Groups IIA, IIIA, IVA, IB, IIB, IIIB, IVB, VIB and VIII of the Periodic Table of the Elements.

14. A synthetic crystalline aluminosilicate zeolite comprising the zeolite of claim 6 having its original cations replaced, at least in part, with a cation or a mixture of cations selected from the group consisting of hydrogen and hydrogen precursors, rare earth metals and metals from Groups IIA, IIIA, IVA, IB, IIB, IIIB, IVB, VIB and VIII of the Periodic Table of the Elements.

15. A synthetic crystalline aluminosilicate zeolite comprising the zeolite of claim 7 having its original cations replaced, at least in part, with a cation or a mixture of cations selected from the group consisting of hydrogen and hydrogen precursors, rare earth metals and metals from Groups IIA, IIIA, IVA, IB, IIB, IIIB, IVB, VIB and VIII of the Periodic Table of the Elements.

16. A synthetic crystalline aluminosilicate zeolite comprising the zeolite of claim 8 having its original cations replaced, at least in part, with a cation or a mixture of cations selected from the group consisting of hydrogen and hydrogen precursors, rare earth metals and metals from Groups IIA, IIIA, IVA, IB, IIB, IIIB, IVB, VIB and VIII of the Periodic Table of the Elements.

17. The synthetic crystalline aluminosilicate zeolite of claim 10 wherein said replacing cation is hydrogen or a hydrogen precursor.

18. A method for preparing the crystalline aluminosilicate zeolite defined in claim 1 which comprises preparing a mixture containing sources of a sodium oxide, cesium oxide, choline chloride, aluminum oxide, silicon dioxide and water and having a composition, in terms of mole ratios of oxides, falling within the following ranges:

$R^+/(R^+ + Na^+ + Cs^+) = 0.2-0.7$
$OH^-/SiO_2 = 0.3-0.7$
$H_2O/OH^- = 15-100$
$SiO_2/Al_2O_3 = 8-25$
$Cs_2O/(Na_2O + Cs_2O) = 0.1-1.0$ wherein R is choline chloride, and maintaining the mixture at a temperature of above 80° C. until crystals of said zeolite are formed.

19. The method of claim 18 wherein the temperature is maintained between about 80° C. and about 220° C.

20. The method of claim 18 wherein the temperature is maintained between about 120° C. and about 150° C.

* * * * *

UNITED STATES PATENT AND TRADEMARK OFFICE
CERTIFICATE OF CORRECTION

PATENT NO. : 4,209,499
DATED : June 24, 1980
INVENTOR(S) : Mae K. Rubin, Edward J. Rosinski, Charles J. Plank It is certified that error appears in the above-identified patent and that said Letters Patent are hereby corrected as shown below:

Column 1, line 35, "Ca, Sr," should read $--\underline{\frac{Ca}{2}}, \underline{\frac{Sr}{2}}, --$.

Column 2, line 9, "$1.0\underline{(}R_2O:Al_2O_3:(5\text{ to }20)\ SiO_2$" should be $--1.\underline{0)}\ R_2O:Al_2O_3:(5\text{ to }20)\ SiO_2--$.

Column 6, line 56, "pressure" should read --pressures--.

Signed and Sealed this

Seventh Day of October 1980

[SEAL]

Attest:

SIDNEY A. DIAMOND

Attesting Officer     Commissioner of Patents and Trademar